United States Patent [19]
Johnson

[11] Patent Number: 6,137,571
[45] Date of Patent: Oct. 24, 2000

[54] OPTICAL INSTRUMENT

[75] Inventor: Mark Johnson, Cheshire, United Kingdom

[73] Assignee: United Utilities PLC, United Kingdom

[21] Appl. No.: 09/125,596

[22] PCT Filed: Mar. 26, 1997

[86] PCT No.: PCT/GB97/00857

§ 371 Date: Apr. 22, 1999

§ 102(e) Date: Apr. 22, 1999

[87] PCT Pub. No.: WO97/36167

PCT Pub. Date: Oct. 2, 1997

[30] Foreign Application Priority Data

Mar. 26, 1996 [GB] United Kingdom .................. 9606367

[51] Int. Cl.[7] ............................................. G01N 1/10
[52] U.S. Cl. ........................................ 356/246; 356/440
[58] Field of Search .................................. 356/246, 410, 356/440

[56] References Cited

U.S. PATENT DOCUMENTS

| | | | |
|---|---|---|---|
| 4,413,504 | 11/1983 | Voigtman et al. | 73/61.1 |
| 4,477,186 | 10/1984 | Carlson | 356/246 |
| 4,488,814 | 12/1984 | Johnson | 356/414 |
| 4,919,899 | 4/1990 | Herrmann et al. | 422/245 |
| 4,943,735 | 7/1990 | Nishikawa | 250/573 |
| 5,030,010 | 7/1991 | Birkle | 356/445 |
| 5,194,915 | 3/1993 | Gilby | 356/318 |
| 5,290,705 | 3/1994 | Davis | 436/164 |

FOREIGN PATENT DOCUMENTS

| | | | |
|---|---|---|---|
| 0666472A2 | 8/1995 | European Pat. Off. | G01N 1/14 |
| 3405592A1 | 8/1985 | Germany | G01N 21/59 |
| 3704960A1 | 8/1988 | Germany | G01N 21/55 |
| 2092758A | 8/1982 | United Kingdom . | |
| WO96/16326 | 5/1996 | WIPO | G01N 21/25 |

Primary Examiner—Frank G. Font
Assistant Examiner—Layla Lauchman
Attorney, Agent, or Firm—Michael Best & Friedrich LLP

[57] ABSTRACT

An instrument for monitoring the characteristics of a liquid comprises a source of radiation (6) which is transmissible through the liquid and a detector (2) for detecting radiation emerging from the liquid. The detector (2) is responsive to components of the emerging radiation which are affected by variations in the characteristics of the liquid. The source (6) and detector (2) are arranged such that the radiation is transmitted through at least one free surface of the liquid (5) which is supported at least in part by surface tension of the liquid.

11 Claims, 2 Drawing Sheets

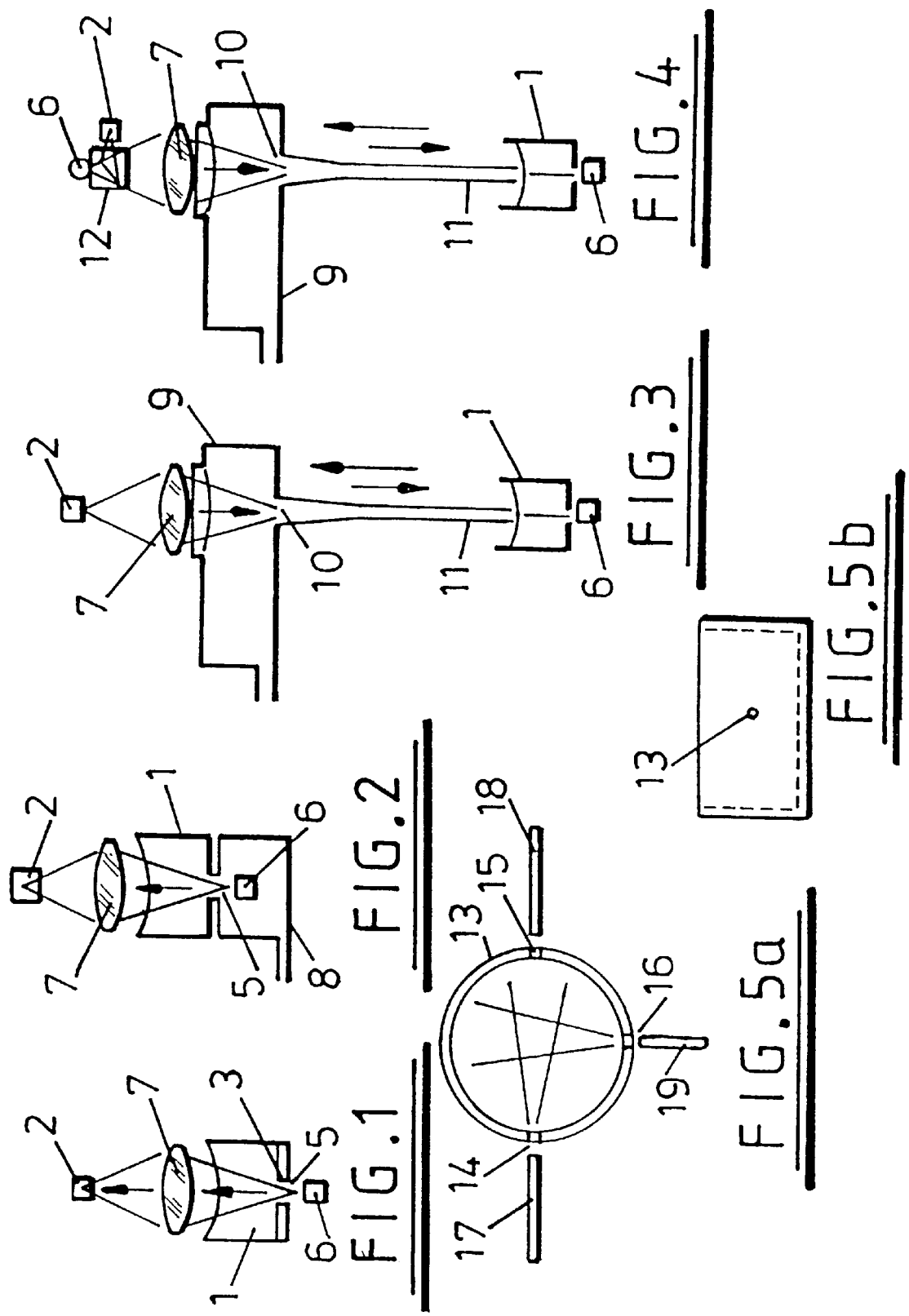

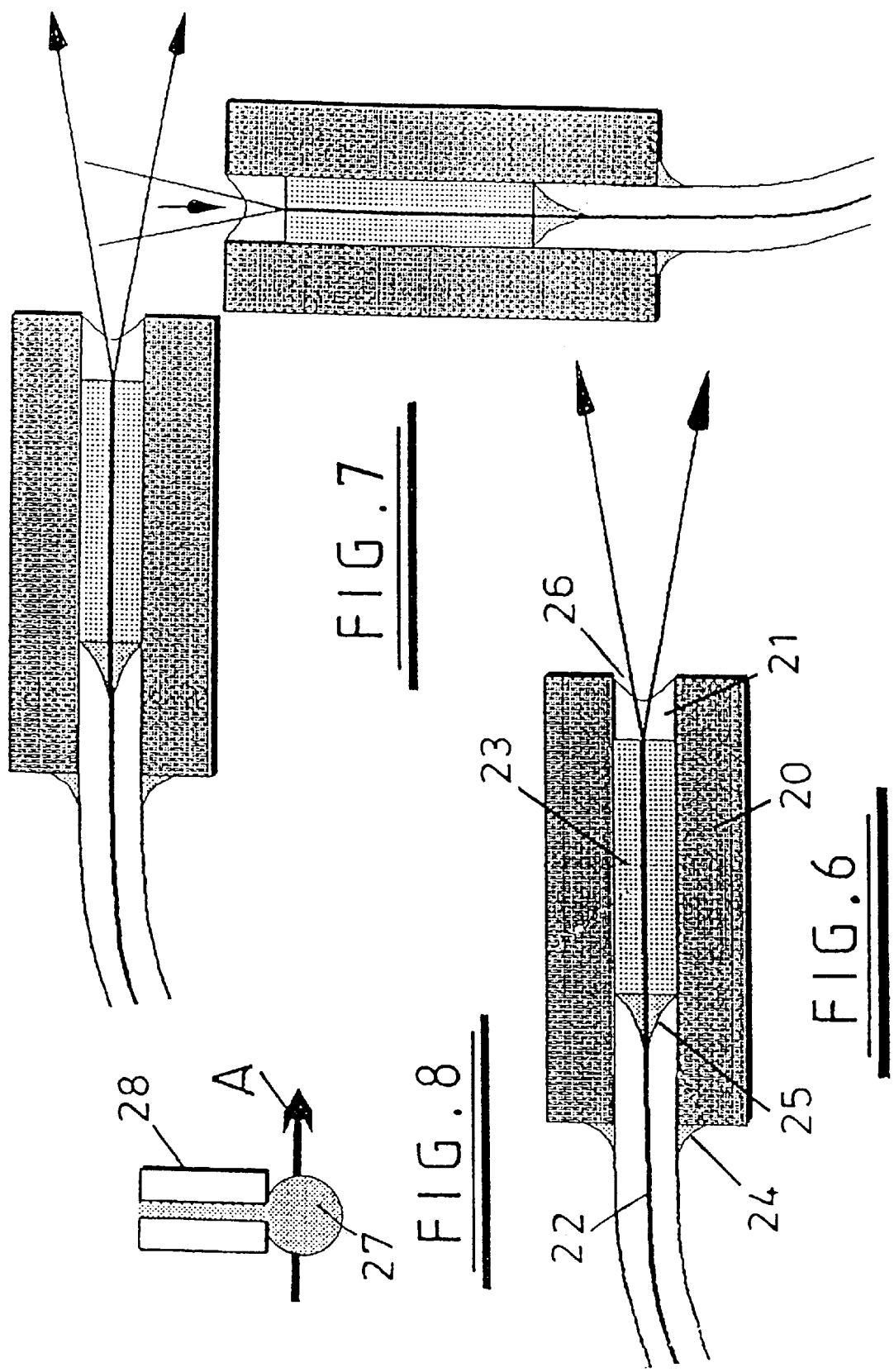

OPTICAL INSTRUMENT

The present invention relates to an instrument for monitoring characteristics of a liquid, such as water.

It is known to use optical techniques for physical and chemical analysis of liquids, including monitoring the quality of water. Typically, a beam of light is shone into a sample of the liquid and transmitted or scattered components of the light are detected and analysed. Such systems may utilise a variety of effects to measure a particular characteristic of the liquid, including measuring absorption, scattering, refractive index, and polarisation properties.

Whatever the analysis technique used, transmitting light in to and out of the liquid sample poses practical problems. In conventional systems the light typically enters and exits the sample via transparent windows which are in direct contact with the liquid. It is therefore important for the efficient and reliable operation of such systems that the windows are kept free from damage, fouling and condensation. Whilst not being particularly problematical in a laboratory environment, degradation of the optical quality of such windows is a fundamental problem encountered with practical industrial measurement systems. Known provisions for the protection or cleaning of windows in such systems are often only partially effective and introduce problems of complexity and unreliability.

It is an object of the present invention to obviate or mitigate the above problems.

According to the present invention there is provided an instrument for monitoring the characteristics of a liquid, comprising a source of radiation which is transmissible through the liquid, means for directing a beam of the radiation from the source through a sample of the liquid, and means for detecting radiation emerging from the liquid, the detector being responsive to components of the emerging radiation which are affected by variations in the characteristics of the liquid, wherein he source and detector are arranged such that the radiation is transmitted through at least one free surface of the liquid which is supported at least in part by surface tension of the liquid.

The present invention also provides a method for monitoring the characteristics of a liquid, comprising directing a beam of radiation through a sample of the liquid and detecting components of the emerging radiation which are affected by variations in the characteristics of the liquid, wherein the radiation is transmitted through at least one free surface of the liquid which is supported at least in part by surface tension of the liquid.

The at least one free surface of the liquid is preferably defined by a meniscus formed at an aperture through which radiation may be transmitted.

In one embodiment of the invention, the aperture is defined by a container which contains at least part of the sample of the liquid. Means may be provided for applying differential pressure between opposite sides of the aperture to provide support for the free surface.

The aperture may be defined in the base of the container and the beam of radiation directed up through it. Alternatively, the aperture may, for instance, be defined in a side wall of the container and the beam of radiation directed substantially horizontally there through.

The container may be a pipe through which the liquid is flowing.

In one embodiment of the invention in which the aperture is defined in a base of a container, means are provided for forming an unsupported thread of the liquid above said container, and the radiation is directed into the thread and guided to the container along the length of the thread by total internal reflection.

In an alternative embodiment of the invention, a drop of the liquid sample is retained by surface tension outside the aperture, and the radiation is directed transversely into the drop.

Rather than being defined by a container containing liquid, the aperture could be defined by a bore such that the meniscus prevents liquid from flowing into the bore. This arrangement is particularly suited for instrument adapted to be immersed in the liquid sample.

It will be appreciated that the detector may be positioned relative to the source to monitor transmitted, transversely scattered, or back-scattered components of the emerging radiation. Also, more than one source and/or detector could be provided to enable various different components of the emerging light to be monitored. For instance, detectors could be positioned to monitor both transmitted and back-scattered radiation.

Specific embodiments of the present invention will now be described, by way of example only, with reference to the accompanying drawings, in which:

FIG. 1 illustrates an optical instrument in accordance with a first embodiment to the present invention;

FIG. 2 illustrates a modification of the instrument illustrated in FIG. 1;

FIG. 3 illustrates a further modification of the instrument illustrated in FIG. 1;

FIG. 4 illustrates a modification of the instrument illustrated in FIG. 3;

FIGS. 5a and 5b illustrate a further embodiment of the present invention;

FIG. 6 illustrates an instrument in accordance with the present invention adapted to be immersed in a liquid sample;

FIG. 7 illustrates use of two of the instruments of FIG. 6; and

FIG. 8 illustrates a simple instrument in accordance with the present invention.

Referring to FIG. 1, a sample of liquid such as water is held ill an open topped container 1, above which is located an optical detector 2. A small aperture 3 is defined in the base of the container, which is fabricated from a non-wetting material. At the aperture 3 the water forms a meniscus 5 which defines a curved surface below the container 1.

An optical source 6 is located directly below the aperture 3 to direct light up through the meniscus 5 and aperture 3 and into the container 1. Light transmitted through the liquid within the container 1, and out through the open top of the container 1, is focused on the detector 2 by coupling optics represented by a lens 7.

Characteristics of the liquid within the container 1 (such as information relating to pollutants) can be monitored by extraction of appropriate information from the detected transmitted light, without that light having to pass through any physical windows which might become damaged or fouled, or limit the light-warelengths possible. That is, the light both enters and leaves the liquid sample through free surfaces of the liquid.

The meniscus 5 provides a transparent port of very high optical quality and also has a small positive optical power. The optical power of the meniscus can be used to modify the angular deviation of light transmitted therethrough. Furthermore, although the aperture 3 will generally be relatively small, the curvature of the meniscus 5 provides a large angular acceptance (approaching $2\pi$ steradians) so that the aperture 3 has a large optical throughput. If required, optical throughput could be increased by providing an array of apertures 3 over an essentially unlimited surface area.

It will be appreciated that if the head of water within the container 1 is such that the pressure within the container 1 exceeds a certain limit relative to the pressure below the container 1, the force on the meniscus 5 will overcome the surface tension and water will simply flow through the aperture 3. It is, however, possible to contain a sufficiently large body of water within the container 1 (without it pouring through the aperture 3) to provide a large enough optical path for the transmitted light to yield useful measurements. For example, tests have shown that a 50 mm diameter cylinder with a 75 μm thick polyester base provided with a 0.52 mm aperture, can hold water at a depth of about 45 mm without it pouring through the aperture. At this depth the meniscus was approximately hemispherical.

The maximum possible head of water that can be held within the container 1 may be simply calculated from the diameter of the aperture 3, the surface tension, and the contact angles of water, base and air (the result is essentially the same as that for capillary rise in a tube).

The depth of water that can be held within the container 1 without it pouring through the aperture 3 could be increased by appropriate control of the pressure on either side of the aperture 3. For instance, referring to FIG. 2, the optical source 6 could be housed within a pressurised enclosure 8 below the container 1. By increasing the pressure within the enclosure 8 it is possible to increase the possible maximum head of water within the container 1 and also to control the curvature of the meniscus 5. Similarly, provision of the pressurised enclosure 8 makes it possible for the diameter of the aperture 3 to be increased.

A further possible modification of the instrument of FIG. 1 is illustrated in FIG. 3, in which water is fed to a header tank 9 located above the container 1, between the container 1 and the lens 7. Water from the header tank 9 falls to the container 1 through an aperture 10 in its base in the form of a continuous thread 11. The water thread 11, although not stable, is capable of transmitting light (from light source 6) from the container 1 to the detector 2 via the header tank 9 and the lens 7. In this way, the optical path of the transmitted light is substantially increased (the thread being for example 150 mm in length).

With the arrangement of FIG. 3, and with the arrangements of FIGS. 1 and FIGS. 2, the locations of the detector 2 and source 6 could be interchanged with one another. Furthermore, referring to FIG. 4, which illustrates a modification of the instrument of FIG. 3, the detector 2 could be replaced by an arrangement combining a detector 2. a source 6, and a beam-splitter 12. In this case, the lens 7 focuses light from the source 6 onto the aperture 10 in the base of the header tank 9 thus directing a beam of light into the water thread 11. Light back-scattered along the water thread 11 is then directed to the detector 2 by the beam-splitter 12. This system could thus, for instance, rely upon the Raman effect (or simple Rayleigh scattering) to measure characteristics of the water. That is, inputting an excitation beam of sufficiently high power causes the formation of a frequency-shifted beam due to scattering of the input beam off dissolved molecules with Raman-active mechanical vibrations. Such frequency-shifted photons are emitted isotropically, and hence can be detected after travelling back along the water thread. The beam-splitter arrangement thus enables the instrument to perform a Raman scattering measurement without any optical component being required in contact with the water.

An alternative embodiment of the invention in which light is introduced into the water sample horizontally rather than vertically is illustrated in FIGS. 5a and 5b (5a being a plan view of 5b). In this example, the water is contained within a cylindrical container such as a pipe 13. Three apertures 14, 15 and 16 are provided within the wall of the pipe at the same vertical height. At each of the three apertures the water forms a meniscus in essentially the same way as described above. An optical source 17 (e.g. an LED or optical fibre etc.) is positioned at the aperture 14 to shine a beam of light into the water sample. Detectors 18 and 19 are positioned at each of the apertures 15 and 16 to detect components of the input light beam which are either transmitted through the water sample (detector 18) or are scattered through 90° (detector 19). This arrangement is particularly useful for monitoring the characteristics of water passing through a pipe line, without having to remove a sample of the water from the pipe line.

Another embodiment of the invention which is useful for conducting in situ measurement is illustrated in FIG. 6. This shows an immersion probe comprising a cylindrical outer casing 20 of non-wetting material defining a narrow internal bore 21. A cladded optical fibre 22 extends into one end of 21 and terminates at a fibre ferrule 23. Adhesive seals are provided at locations indicated by references 24 and 25. In use the probe is immersed in a body of liquid which will form a meniscus 26 at the opening of the bore 21. A light beam can then be introduced into the liquid from the optical fibre, passing through the meniscus 26. Similarly, back scattered light from the liquid is transmitted through the meniscus 26 and then to a detector(not shown), via the optical fibre 22.

By using two or more such probes, as illustrated in FIG. 7, components of the introduced light beam scattered through other angles (such as 90° as with the arrangement shown in FIG. 7) can be monitored. Similarly, by facing two such probes towards one another components of light transmitted through the liquid without scattering can also be measured.

With all the above described embodiments of the invention there is no requirement for a physical window to transmit light to or from the liquid sample. Should the apertures used to define the meniscus ports become fouled, which is unlikely, they can readily be cleaned, with, for instance, a pulse of air. Indeed, periodic ejection of air bubbles is seen as being a most useful way to inhibit the growth of biofilms around the aperture.

A further embodiment of the invention is illustrated in FIG. 8. This is a simple embodiment in which a liquid drop 27 is simply suspended from a capillary tube 28 such that light can be transmitted transversely through the drop, for instance in the direction of arrow A. By appropriate positioning of optical sources and detectors (not shown) components of transmitted and/or scattered light can be measured. This arrangement offers the potential advantage that only a very small volume of liquid is required. However, it suffers the disadvantage that the maximum optical path is limited by the size of the drop 27 to only a few millimeters in most practical situations.

It will be appreciated that all the above embodiments of the invention can be used for monitoring the characteristics of a wide variety of liquids including, but not limited to, water. It will also be appreciated that many modifications could be made to the detail of the various arrangements such as the choice of optical components etc. Other possible modifications will be evident to the appropriately skilled person.

What is claimed is:

1. An instrument for monitoring the characteristics of a liquid, comprising a source of radiation which is transmissible through the liquid, means for directing a beam of the radiation from the source through a sample of the liquid, and means for detecting radiation emerging from the liquid, the detector being responsive to components of the emerging radiation which are affected by variations in the characteristics of the liquid, wherein at least a part of the liquid sample is contained in a container which is provided with at least one aperture exposing a free surface of the liquid defined by a meniscus formed at the aperture, and the source and detector are arranged such that the radiation is transmitted through the aperture and into the sample contained by the container.

2. An instrument according to claim 1, wherein means are provided for applying differential pressure between opposite sides of said aperture to provide support for the at least one free surface.

3. An instrument according to claim 2, wherein said means comprises means for raising the pressure in the region of the aperture outside the container above the pressure in the region of the aperture inside the container.

4. An instrument according to claim 3, wherein said means comprises a pressurised enclosure positioned around the aperture.

5. An instrument according to claim 1, wherein said aperture is defined in a base of said container, radiation being directed substantially vertically through the aperture.

6. An instrument according to claim 5, wherein means are provided for forming an unsupported thread of the liquid above said container, and wherein the radiation is directed into the thread and guided to the container along the length of the thread by total internal reflection.

7. An instrument according to claim 1, wherein an aperture is defined in a substantially vertical side wall of the container and radiation is directed substantially horizontally through the aperture.

8. An instrument according to claim 1, wherein a detector is positioned to monitor transmitted components of the emerging radiation.

9. An instrument according to claim 1, wherein a detector is positioned to monitor components of the emerging radiation that have been transversely scattered.

10. An instrument according to claim 1, wherein a detector is positioned to monitor back-scattered components of the emerging radiation.

11. A method of monitoring the characteristics of a liquid, comprising directing a beam of radiation through a sample of the liquid and detecting components of the emerging radiation which are affected by variations in the characteristics of the liquid, wherein at least a part of the sample is contained within a container provided with at least one aperture exposing a free surface of the liquid defined by a meniscus supported within the aperture, and the radiation is transmitted through the aperture and into the liquid within the container.

* * * * *